(12) United States Patent
Freehauf et al.

(10) Patent No.: US 10,231,472 B2
(45) Date of Patent: Mar. 19, 2019

(54) ZILPATEROL ANIMAL PREMIX FORMULATION

(71) Applicant: Intervet Inc., Madison, NJ (US)

(72) Inventors: Keith Freehauf, Stockton, NJ (US);
Brian Carrillo, Jackson, NJ (US);
Jiyue Zhang, Edison, NJ (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/743,799

(22) PCT Filed: Jul. 20, 2016

(86) PCT No.: PCT/EP2016/067273
§ 371 (c)(1),
(2) Date: Jan. 11, 2018

(87) PCT Pub. No.: WO2017/013167
PCT Pub. Date: Jan. 26, 2017

(65) Prior Publication Data
US 2018/0199595 A1    Jul. 19, 2018

Related U.S. Application Data

(60) Provisional application No. 62/195,099, filed on Jul. 21, 2015.

(51) Int. Cl.
| | |
|---|---|
| *A23K 20/137* | (2016.01) |
| *A23K 20/105* | (2016.01) |
| *A23K 50/10* | (2016.01) |
| *A61K 31/55* | (2006.01) |
| *A23K 10/37* | (2016.01) |
| *A23K 20/111* | (2016.01) |
| *A23K 20/163* | (2016.01) |
| *A23K 20/28* | (2016.01) |
| *A23K 50/75* | (2016.01) |
| *A61K 9/16* | (2006.01) |

(52) U.S. Cl.
CPC ............ *A23K 20/137* (2016.05); *A23K 10/37* (2016.05); *A23K 20/105* (2016.05); *A23K 20/111* (2016.05); *A23K 20/163* (2016.05); *A23K 20/28* (2016.05); *A23K 50/10* (2016.05); *A23K 50/75* (2016.05); *A61K 9/167* (2013.01); *A61K 31/55* (2013.01); *Y02P 60/877* (2015.11)

(58) Field of Classification Search
CPC ..... A23K 20/137; A23K 20/105; A23K 50/10
See application file for complete search history.

(56) References Cited

U.S. PATENT DOCUMENTS

| | | |
|---|---|---|
| 4,585,770 A | 4/1986 | Frechet et al. |
| 4,900,735 A | 2/1990 | Grandadam |
| 5,731,028 A | 3/1998 | Chevremont et al. |
| 5,847,124 A | 12/1998 | Chevremont et al. |

FOREIGN PATENT DOCUMENTS

| | | |
|---|---|---|
| EP | 0197188 A1 | 10/1986 |
| EP | 0753518 A1 | 1/1997 |
| WO | 2009002558 A1 | 12/2008 |
| WO | 2013171330 A1 | 11/2013 |
| WO | 2014140237 A1 | 9/2014 |

OTHER PUBLICATIONS

Elanco Animal Health, Ractopamine Hydrochloride (Optaflexx™ 45) Type A Medicated Article for Beef Cattle, Freedom of Information Summary—Original New Animal Drug Application NADA 141-221, 2003, Approval Date: Jun. 13, 2003, pp. 1-29.
International Search Report for application PCT/EP2016/067273 dated Aug. 23, 2016, 12 pages.
Intervet Inc., Zilmax (Zilpaterol Hydrochloride)—Type A Medicated Article for Cattle Fed in Confinement for Slaughter, Freedom of Information Summary—Original New Animal Drug Application NADA 141-258, 2006, Approval Date: Aug. 10, 2006, pp. 1-43.

*Primary Examiner* — Theodore R. West

(57) ABSTRACT

A new solid dosage form formulation and manufacturing process incorporating zilpaterol HCl is presented. This formulation is an animal feed premix with improved content uniformity and is manufactured by a simple method that uses a supersaturated solution of zilpaterol that is incorporated into a solid carrier matrix.

20 Claims, No Drawings

ZILPATEROL ANIMAL PREMIX FORMULATION

CROSS-REFERENCE TO RELATED APPLICATIONS

This application is a national stage entry under 35 U.S.C. § 371 of PCT/EP2016/067273, filed on Jul. 20, 2016, which claims priority to U.S. Application No. 62/195,099, filed on Jul. 21, 2015, the content of 62/195,099 is hereby incorporated by reference in its entirety.

BACKGROUND OF THE INVENTION

Zilpaterol is a known adrenergic β-2 agonist corresponding in structure to Formula (I):

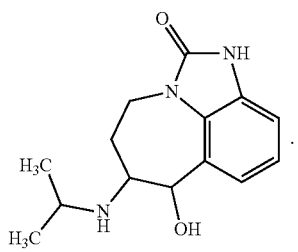

(I)

The IUPAC name for zilpaterol is 4,5,6,7-tetrahydro-7-hydroxy-6-(isopropylamino) imidazo[4,5,1-jk]-[1]benzazepin-2(1H)-one. The Chemical Abstracts name for zilpaterol is 4,5,6,7-tetrahydro-7-hydroxy-6-[(1-methyl-ethyl)amino]-imidazo[4,5,1-jk][1]benzazepin-2(1H)-one.

Zilpaterol hydrochloride is sold by Merck Animal Health, under the trademark ZILMAX®. It is approved in the United States for increased rate of weight gain, improved feed efficiency, and increased carcass leanness in cattle fed in confinement for slaughter during the last 20 to 40 days on feed. The approved inclusion rate of zilpaterol hydrochloride is 6.8 grams/ton (7.5 ppm) in feed (see Freedom of Information Summary for NADA 141-258, approved Aug. 10, 2006).

In U.S. Pat. No. 4,585,770, Fréchet et al. discuss compounds, such as zilpaterol, encompassed by a genus characterized as 6-amino-7-hydroxy-4,5,6,7-tetrahydro-imidazo[4,5,1-j-k][1]-benzazepin-2-(1H)-one derivatives and acid addition salts thereof.

In U.S. Pat. No. 4,900,735, Grandadam discusses a zootechnical composition comprising zilpaterol and acid addition salts thereof. Grandadam states that such a composition may be used in general to increase the weight of cattle, pigs, sheep, and poultry.

In U.S. Pat. Nos. 5,731,028 and 5,847,124, Chevremont et al. discuss crystallized anhydrous zilpaterol hydrochloride, and particularly crystallized anhydrous zilpaterol hydrochloride wherein less than 5% of the crystals have a size of less than 15 μm, and at least 95% of the crystals have a size of less than 250 μm. According to Chevremont et al., such crystals may be incorporated into animal feed to increase body weight and meat quality. Chevremont et al. provide methods for making such crystals, and discuss using the crystals to make animal premixes in which the crystals are secured to a corn cob support having a greater particle size.

WO2013/171330 discloses a method of enhancing the performance of broiler chickens using zilpaterol containing feed.

WO2014/140237 discloses a method of improving the efficiency of beef production from bovine animals which comprises feeding zilpaterol to the animals.

EP0197188 describes a method of preparing non dusty blend of meals or flours with additives for use in fodder manufacturing and or for livestock feeding. Specifically, the method involves the blending of the meal or flour with a nonionic physiologically compatible surfactant such as esters of propylene glycol. The active ingredient exemplified is Carbadox. Zilpaterol is not disclosed.

Ractopamine hydrochloride is sold by Elanco Animal Health under the trademark Optaflexx®. It is approved in the United States for increasing the rate of weight gain, improving feed efficiency in cattle fed in confinement for slaughter during the last 28 to 42 days on feed. The approved inclusion rate of ractopamine hydrochloride is 10 to 30 ppm (see Freedom of Information Summary for NADA 141-221, approved Jun. 13, 2003).

SUMMARY OF THE INVENTION

An embodiment of the invention is an animal feed premix comprising
    zilpaterol or a salt thereof in the range of 0.5 to 2.0%;
    propylene glycol in range of 5-10%; and
    a solid carrier.
In another embodiment, the animal feed premix further comprises water in the range of 1-4%.
In another embodiment, the zilpaterol is zilpaterol HCl.
In another embodiment, the solid carrier is selected from the group consisting of corn cobs, rice hulls, sugar, maltodextrins, talc, cellulose or mixtures thereof.
In yet another embodiment, the solid carrier is corn cobs.
An embodiment of the invention is a process for preparing the animal feed premix comprising
    a) mixing the zilpaterol and propylene glycol so that the zilpaterol concentration is higher than the concentration that can be completely dissolved in the propylene glycol at room temperature;
    b) heating the mixture of step a) until all zilpaterol goes into solution; and hereby creating a supersaturated solution of zilpaterol
    c) mixing the zilpaterol solution of step b) with the solid carrier.
In an additional embodiment, the process of preparing the animal feed premix further comprises adding water to the zilpaterol, propylene glycol mixture of step a)
An embodiment of the invention is an animal feed premix comprising
    0.5-2.0% zilpaterol HCl;
    5-10% propylene glycol;
    1-4% water; and
    QS milled corn cobs.
An embodiment of the invention is a method of preparing a medicated animal feed comprising mixing the animal feed premix with grain or other conventional animal feed on grain basis (e.g. pellets).
In an additional embodiment of the method of preparing a medicated animal feed, that comprises zilpaterol homogeneously mixed therein, the relative standard deviation (RSD) value of the distribution of the zilpaterol in the feed prepared from the premix is less than 15%.
In an additional embodiment of the method of preparing an animal feed, the RSD of the distribution of the zilpaterol in the feed is less than 10%.

In an additional embodiment of the method of preparing an animal feed, the RSD of the distribution of the zilpaterol in the feed is less than 5%.

In an embodiment, the invention is a use of the animal feed premix in a method of preparing a homogenous medicated feed to administer lower concentrations than 7.5 ppm of zilpaterol to animals.

In another embodiment, the concentration of zilpaterol in the medicated feed is 4 ppm or less.

DETAILED DESCRIPTION

A new solid dosage form formulation and manufacturing process incorporating zilpaterol HCl is presented. This formulation is an animal feed premix for preparing medicated feed with improved content uniformity and is manufactured by a simple method that uses a supersaturated solution of zilpaterol that is incorporated by absorption into a solid carrier matrix.

The zilpaterol HCl used in the current zilpaterol premix product, Zilmax®, is manufactured to a specific particle size range wherein less than 5% of the crystals have a size of less than 15 μm, and at least 95% of the crystals have a size of less than 250 μm. In order to achieve this range, a number of manufacturing steps are required. It is costly to manufacture the API to these requirements. The zilpaterol HCl is then formulated into a finished product (premix) by adding solid API to a solid a carrier that is treated with excipients designed to adhere the drug physically to the carrier with the solid API in suspension in the excipients.

This process has the disadvantages of being expensive because of the added safety needed to handle solid zilpaterol HCl and the dust that can be generated. The process also takes time to complete.

An additional disadvantage of this existing formulation is that it does not mix uniformly into feed at concentrations at or below 4 ppm. The current manufacturing process, while effective for the current product which has a zilpaterol concentration of 4.8% as a premix and is used to produce feed with a zilpaterol concentration of 6.8 g/ton or 7.5 ppm, was not effective in producing a premix product that could be used to produce a feed with uniform distribution of zilpaterol in a feed at concentrations of 4 ppm or below. The relative standard deviation (RSD) of feed prepared from a zilpaterol formulation with zilpaterol concentration of 4 ppm and manufactured as described is 71.9%. Typically, a feed should have a RSD of less than 10%.

The claimed product and process eliminates the need for a specific particle size for the zilpaterol HCl. This is accomplished by dissolving the zilpaterol in a solvent and combining the resultant zilpaterol solution with solid support, with good absorptive properties instead of the suspension used in the current product.

However, this approach raises an additional issue: excess moisture in the premix formulation. Use of an excessive amount of solvent can produce a premix that has poor physical properties such as caking or unacceptable flowability based on the stickiness of the solvent. Furthermore, medicated premixes have a tendency to cake/lump with prolonged storage. One possible solution would be to evaporate the excess moisture through heat and/or pressure. However, this would increase the expense and time to manufacture the product.

Applicants have found that a supersaturated solution of zilpaterol can be used to produce a feed premix product with the desired physical properties which can also produce a medicated feed with a uniform distribution of zilpaterol in concentrations of 4 ppm or below. Desired physical properties include but are not limited to the formulation has reduced or no dust, is flowable, has little or no mold and no undesirable odors.

The use of a supersaturated solution avoids an excess of solvent/liquid in the product and thereby eliminates the need to dry the material and prevents stickiness. This allows for a less expensive and simplified method of manufacture of the zilpaterol feed premix. This new formulation also addresses issues with the cost of controlling the particle size of the zilpaterol and it addresses safety issues by minimizing the use of powder/solid zilpaterol in the manufacture and use of the finished formulation.

In one embodiment, the drug is a salt of zilpaterol such as zilpaterol hydrochloride or zilpaterol HCl.

Such manufacturing process and premix formulation are described for zilpaterol but they can be used as well for other β adrenergic substances, such as ractopamine or the compounds disclosed in WO 2008/044127 or in feed premix products that comprise a combination of other drugs in combination with zilpaterol. Minor modifications of the manufacturing processes might be necessary to adapt to such a compound. Such modifications are, however part of the knowledge of the skilled person. Final drug concentrations of 0.1-15% in the feed premix can be prepared depending on the drug without the need for a drying step.

Propylene glycol is the preferred solvent. Other non-aqueous solvents or combination of non-aqueous solvent and water solvent can be used with propylene glycol comprising the major liquid constituent.

Milled corn cobs are the preferred carrier. Other dry carriers can be used including rice hulls and other grain materials with good absorptive properties. Other carries like sugars/maltodextrins, talc, celluloses etc. can be used alternatively, as long as they have similar absorptive properties. It is also possible to use a combination of such carriers. The choice of the carriers is determined by its adsorptive properties and the physical characteristics to allow homogeneous mixing with grain or other conventional feed material in order to form a medicated feed.

Other additives can be included in either the zilpaterol solution phase or solid carrier including colorants, preservatives, buffers, glidants, stabilizers, crystallization inhibitors. An example of a crystallization inhibitor is polyvinylpyrrolidone (PVP).

The medicated feed that is produced with the feed premix according to the current invention is especially useful for improving the growth of meat producing animals, such as poultry animals, e.g. chickens, especially broiler chickens or cattle, especially beef cattle.

The feed premix according to this invention or that is produced with the method according to the invention can be a Type A Medicated Feed, a Type B Medicated Feed as defined in US 21 CFR § 558.3.

The feed premix according to this invention or that is produced with the method according to the invention can be used (by dilution) to prepare a Type A Medicated Feed, a Type B Medicated Feed or a Type C Medicated Feed as defined in US 21 CFR § 558.3.

Feed means edible materials which are consumed by animals and contribute energy and/or nutrients to the animals' diet (American Association of Feed Control Officials, $5^{th}$ Ed. 2014, p 178).

Medicated feed is any feed which contains drug ingredients intended or presented for the cure, mitigation, treatment, or prevention of disease of animals other than man or which contains drug ingredients intended to affect the structure or any function of the body of animals other than man (American Association of Feed Control Officials, 5th Ed., p 187).

Coefficient of variation (CV) is standard deviation of the zilpaterol concentration of the samples taken divided by the mean of the zilpaterol concentration of the samples time 100. See Herman, et al., Testing Mixer Performance, MF-1172 Kansas State University Agricultural Experiment Station and Cooperative Extension Service, October 1994. This term is also known as Relative Standard Deviation (RSD). With respect to medicated feeds, a lower RSD is indicative of a more uniform distribution of the drug within the feed. This ensures that each animal in each mouthful gets the same amount of drug.

The following types of Medicated Products are defined in US 21 CFR § 558.3:

"Type A Medicated Article": (also called Premix) is intended solely for use in the manufacture of another Type A Medicated Article or a Type B or Type C Medicated Feed. It consists of an animal drug(s) with or without a carrier (e.g., calcium carbonate, rice hull, corn, gluten) with or without inactive ingredients.

"Type B Medicated Feed": (Type B feed) (previously called Concentrate) is intended solely for the manufacture of other medicated feeds (Type B or Type C). It contains a substantial quantity of nutrients including vitamins and/or minerals and/or other nutritional ingredients in an amount not less than 25 percent of the weight. It is manufactured by diluting a Type A Medicated Article or another Type B Medicated Feed.

"Type C Medicated Feed": (Type C feed) is intended as the complete feed for the animal or may be fed "top dressed" (added on top of usual ration) on or offered "free-choice" (e.g., supplement) in conjunction with other animal feed. It contains a substantial quantity of nutrients including vitamins, minerals, and/or other nutritional ingredients. It is manufactured by diluting a Type A Medicated Article or a Type B Medicated Feed. A Type C Medicated Feed may be further diluted to produce another Type C Medicated Feed.

Supersaturated is when a solution contains more solute than is normally possible under given conditions of temperature and pressure.

Other definitions for selected terms used herein will be found within the description of the invention and apply throughout. Unless otherwise defined, all other scientific and technical terms used herein have the same meaning as commonly understood by individuals who are skilled in the art.

In an embodiment, a composition of the subject invention is:

| Ingredient | % w/w |
| --- | --- |
| Zilpaterol HCl | 0.8 |
| Water, purified | 2.0 |
| Propylene glycol | 6.0 |
| Corn cobs, milled | QS |

In another embodiment, a method of manufacturing the composition is:
1. In a vessel containing the zilpaterol HCl add a suitable solvent(s). Mix to disperse as needed;
2. Heat the vessel until the zilpaterol HCl goes into solution and the contents become clear;
3. Into a separate vessel, add a dry carrier. While mixing the carrier, add the drug/solvent liquid to the carrier.
4. Continue mixing until free flowing.
5. Discharge and package.

An embodiment of the invention is an animal feed premix comprising
 zilpaterol or a salt thereof in the range of 0.5 to 2.0%;
 propylene glycol in range of 5-10%; and
 a solid carrier.

In another embodiment, the animal feed premix further comprises water in the range of 1-4%.

In another embodiment, the zilpaterol is zilpaterol HCl.

In another embodiment, the solid carrier is selected from the group consisting of corn cobs, rice hulls, sugar, maltodextrins, talc, cellulose or mixtures thereof.

In yet another embodiment, the solid carrier is corn cobs.

In an embodiment, the ratio of the amount of propylene glycol to the amount of water in the premix composition is about 10 to 1 or about 5 to 1 or about 3 to 1 or about 2 to 1 or about 1 to 1.

An embodiment of the invention is a process for preparing the animal feed premix comprising
 a) mixing the zilpaterol and propylene glycol;
 b) heating the mixture of step a) until zilpaterol goes into solution; and
 c) mixing the zilpaterol solution of step b) with the solid carrier.

In an additional embodiment, the process of preparing the animal feed premix further comprises adding water to the zilpaterol, propylene glycol mixture of step a)

In another embodiment, the process of preparing the animal feed premix, the zilpaterol solution of step b) is supersaturated with respect to zilpaterol.

In another embodiment, the mixture of step a) is heated in step b) to a temperature in the range of about 40° C. to about 100° C., or about 40° C. to about 60° C., or about 60° C. to about 80° C., or about 80° C. to about 90° C., or about 70° C. to about 100° C. or about 60° C. to about 100° C.

An embodiment of the invention is an animal feed premix comprising
 0.5-2.0% zilpaterol HCl;
 5-10% propylene glycol;
 1-4% water; and
 QS milled corn cobs.

An embodiment of the invention is a method of preparing an animal feed comprising mixing the animal feed premix with grain.

In an additional embodiment of the method of preparing an animal feed, the relative standard deviation (RSD) value of the distribution of the zilpaterol in the feed prepared from the premix is less than 15% or less than 10% or less than 5%.

In an embodiment, the animal feed is a poultry feed. In an alternative embodiment, the feed contains other feed additives such as vitamins, minerals, growth promoters such as tylosin, monensin and megesterol acetate (MGA) and antiparasitic compounds.

In another embodiment, other additives can be included in either the solution phase or solid carrier including colorants, preservatives, buffers, glidants, stabilizers, crystallization inhibitors. In an embodiment, the crystallization inhibitor is polyvinylpyrrolidone (PVP). In another embodiment, the composition is prepared without a crystallization inhibitor.

In an embodiment, the invention is a use of the animal feed premix in a method of preparing a homogenous medicated feed to administer lower concentrations of zilpaterol to animals.

In another embodiment, the concentration of zilpaterol in the feed is about 4 ppm or less or about 0.5 ppm to about 7 ppm or about 1 ppm to about 4 ppm or about 4 ppm to about 7 ppm or is about 1 ppm or is about 2 ppm or is about 3 ppm or is about 4 ppm or is about 5 ppm or is about 6 ppm or is about 7 ppm.

EXAMPLES

For some drugs that have a good solubility profile formulations can be prepared by dissolving the drug into a solvent and then mixing the resulting solution with additional excipient/carriers to prepare a suitable dosage form (premix, tablets, etc.). This approach works best when the drug concentration is very low and the drug has good solubility. If an excess amount of liquid is added during manufacture a wet mass can be formed that is difficult to process and needs to be dried to remove excess solvent. Drying adds additional cost and complexity to the manufacturing process. Zilpaterol HCl has a very good solubility of 130 mg/ml in water but only 2.9% solubility in propylene glycol, making water a preferred solvent for the drug.

To manufacture a 0.8% premix it would require approximately 6% water. At a 6% water content, the corn cob carrier would be capable of absorbing the water and remain free flowing without a drying step. This formula and process is very simple and cost effective. When premix material (Sample 38E) was made in the laboratory using approximately 6% water and 2% propylene glycol (as a preservative) the premix showed excellent drug distribution (RSD 0.8%). However, when this premix was used to prepare into feed (Sample 52E) at a final zilpaterol concentration of 2 ppm surprisingly poor results for uniformity were obtained (RSD 19.9%). Multiple experiments were performed trying to increase the amount of water/liquid added and trying different manufacturing techniques such as spraying the liquid on instead of pouring the liquid onto the carrier. All approaches showed poor content uniformity.

Unexpectedly, it was only when the water amount was minimized and a high level of non-aqueous liquid such as propylene glycol was used (Sample 38A) that improved content uniformity (as represented by RSD) was obtained in both premix (RSD 0.8%) and especially in medicated feed (RSD 4.4%) at the low level of 2 ppm (Sample 52A).

When premix was manufactured containing 0.8% zilpaterol HCl, 6% propylene glycol and 2% water it was observed that the drug was not fully soluble. Since increasing the amount of water previously resulted in poor content uniformity, attempts were made to increase the amount of propylene glycol. However since solubility of the drug was poor in propylene glycol, a significant additional amount of propylene glycol was needed (27.6%) to fully solubilize the drug. Since propylene glycol is viscous/sticky, this larger amount of propylene glycol could not be added to the corn cob carrier without causing the product to be sticky which results in poor flow properties. To address this problem, a premix containing only 6% propylene glycol and 2% water was prepared by heating the liquid mixture of zilpaterol HCl to a high temperature and creating a supersaturation of zilpaterol HCl in the propylene glycol/water vehicle. This was successful in fully solubilizing the zilpaterol HCl without needing to add additional liquids. Additionally, the supersaturated solution does not rapidly recrystallize when heat is removed which allows this concentrated solution to be used effectively. Stability in solution at temperatures as high as 90° C. has been demonstrated. When this hot supersaturated solution is added to a dry carrier, it is easily absorbed and mixed and the combination becomes dry and free flowing. Excellent uniformity is obtained, and product safety is improved since free solid drug particles are avoided.

Propylene glycol is the preferred solvent. An improved chemical and physical stability is observed with a combination of propylene glycol and water (102.6% after 45 days at 60° C.) compared to the stability in propylene glycol (95.2% after 45 days at 60° C.) alone. A propylene glycol/water mixture (88754-126-4) has also been shown to have improved stability for the drug compared to a different non-aqueous liquid vehicle polyethylene glycol/water mixture (88754-126-7). Results after high temperature storage of 60° C. for 45 days showed a potency of 102.6% of the propylene glycol/water formulation and potency result of 92.4% for the polyethylene glycol (PEG)/water mixture.

Example 1—Zilpaterol Premix Compositions

Sample 38A Zilpaterol (0.8%) Premix Composition

| MATERIAL | % |
|---|---|
| Zilpaterol HCl | 0.80 |
| Water | 2.00 |
| Propylene glycol | 6.00 |
| Water (rinse) | 0.50 |
| Corn cobs (40/60) | 90.70 |

Corn cobs 40/60 has an average particle size between 0.25-0.42 mm

Propylene glycol and water were added to a bottle and mixed until uniform. The zilpaterol was then added and mixed. The resulting mixture was then heated in an oven at 60° C. until the zilpaterol formed a solution with the propylene glycol and water. The corn cobs were placed in a mixing bowl whose tare weight had been previously determined. The zilpaterol solution was added by pipette to the corn cobs while mixing at mixer speed 1 over 2 min. After the addition of the zilpaterol, the mixture was mixed for an additional 1 min. The bottle was rinsed with water and the rinse water added to the zilpaterol corn cob mixture. The mixture was stirred for 1 minute. The mixer and blade were then brushed down. The mix was stirred for an additional 5 minutes at speed 1.

Premix samples 38 B, C, D, E and F were produced in similar fashion.

Example 2—Medicated Poultry Feed

Sample 52A Medicated Poultry Fee (2% H$_2$O/6% Propylene Glycol on Corn Cobs with 2.0 PPM Zilpaterol HCl 9.0 g of poultry feed was sieved through a 20 μm sieve. The fines were collected in a beaker. The zilpaterol premix (Sample 38A) was added to the beaker and mixed until uniform. 3990 g of poultry feed and the contents of the beaker were combined in a bowl and mixed for 5 minutes. The mixture was then put in a bag and tossed for 1 minute. A 4 kg batch of medicated poultry feed was produced.

Feed samples 52 C, D, E and F were produced in similar fashion.

Example 3—Uniformity of Zilpaterol Concentration in Premix and Feed Samples

The zilpaterol premix samples 38 A-F were subsampled and analyzed for zilpaterol content. These results are presented in Table 1 below.

TABLE 1

Assay Results of Zilpaterol Premix samples

| Sample Number and composition | Conditions/ Time Points | % zilpaterol | Subsample Number | % Assay |
|---|---|---|---|---|
| 38A 2% H$_2$O/6% propylene glycol (PG)/corn cobs (CC) | Room Temperature/ Initial | 0.8% | 1 2 3 | 96.7 95.9 97.5 |
| | Average % RSD | | | 96.7 0.8 |
| 38B 1% H$_2$O/5% PG/rice hulls (RH) | Room Temperature/ Initial | 0.8% | 1 2 3 | 96.3 98.1 99.9 |
| | Average % RSD | | | 98.1 1.8 |
| 38C 2.5% H$_2$O/6% PG/ CC | Room Temperature/ Initial | 1.6% | 1 2 3 | 92.5 96.8 94.6 |
| | Average % RSD | | | 96.4 2.3 |
| 38D 2.5% H$_2$O/5% PG/ RH | Room Temperature/ Initial | 1.6% | 1 2 3 | 92.6 100.4 97.6 |
| | Average % RSD | | | 96.9 4.1 |
| 38E 6% H$_2$O/2% PG/CC | Room Temperature/ Initial | 0.8% | 1 2 3 | 86.2 87.3 86.0 |
| | Average % RSD | | | 86.5 0.8 |
| 38F 1.5% H$_2$O/5% PG/ RH | Room Temperature/ Initial | 0.8% | 1 2 3 | 101.1 100.0 96.3 |
| | Average % RSD | | | 99.1 2.5 |

Poultry Feed Samples 52 A, C, D and E were subsampled and analyzed for zilpaterol content. These results are presented in Table 2 below.

TABLE 2

Assay Results of Zilpaterol Type C Feed samples

| Sample Number | Conditions/ Time Points | Label Claim | Subsample Number | % Assay |
|---|---|---|---|---|
| 52A | Room Temperature/ Initial | 2.0 ppm | 1 2 3 4 5 | 87.1 91.0 96.6 86.8 91.5 |
| | Average % RSD | | | 90.6 4.4 |
| 52C | Room Temperature/ Initial | 2.0 ppm | 1 2 3 4 5 | 84.1 90.3 97.3 97.8 85.0 |
| | Average % RSD | | | 90.9 7.2 |
| 52D | Room Temperature/ Initial | 2.0 ppm | 1 2 3 4 5 | 120.2 135.5 101.7 99.8 109.6 |
| | Average % RSD | | | 113.4 13.1 |
| 52E | Room Temperature/ Initial | 2.0 ppm | 1 2 3 4 5 | 131.5 95.6 118.5 78.0 99.8 |
| | Average % RSD | | | 104.7 19.9 |
| 52F | Room Temperature/ Initial | 2.0 ppm | 1 2 3 4 5 | 96.3 87.2 102.5 93.1 88.9 |
| | Average % RSD | | | 93.6 6.5 |

Example 4—Determination of RSD

Sample 52A was transferred to a bag. 10 g sub-samples were removed from 5 different locations to represent top, top/middle, middle, middle/bottom and bottom of the bag. Each subsample was analyzed for zilpaterol content. The average zilpaterol concentration, the standard deviation (S) and the relative standard deviation (RSD) was determined.

The average zilpaterol concentration of the sample $$\overline{x}$$

was calculated by summing the individual results of each subsample's zilpaterol concentration and dividing this sum by the number (n) of individual values (n=5):

$$\overline{x} = \frac{\Sigma X}{n}$$

The standard deviation (S) was calculated using the following equation:

$$s = \sqrt{\frac{\Sigma(x - \overline{x})^2}{n-1}}$$

The relative standard deviation (RSD) is expressed in percent and was obtained by multiplying the standard deviation by 100 and dividing this product by the average.

RSD=100S/$\overline{x}$

RSD values for Samples 38A-F and 52 C-F were determined by the same method.

The invention claimed is:
1. An animal feed premix comprising
   zilpaterol or a salt thereof in the range of 0.5 to 2.0 w/w %;
   propylene glycol in range of 5-10 w/w %; and
   a solid carrier.
2. The premix of claim 1, further comprising water in the range of 1-4 w/w %.
3. The premix of claim 1, wherein the zilpaterol is zilpaterol HCl.
4. The premix of claim 1, wherein the solid carrier is selected from the group consisting of corn cobs, rice hulls, talc, cellulose or mixtures thereof.
5. The premix of claim 4, wherein the solid carrier is corn cobs.
6. An animal feed premix comprising
   0.5-2.0 w/w % zilpaterol HCl;
   5-10 w/w % propylene glycol;

1-4 w/w % water; and

QS milled corn cobs.

7. A process for preparing the animal feed premix of claim 1 comprising
   (a) mixing the zilpaterol and propylene glycol;
   (b) heating the mixture of step (a) until zilpaterol goes into solution; and
   (c) mixing the zilpaterol solution of step (b) with the solid carrier, thereby obtaining an animal feed premix according to claim 1.

8. The process of claim 7, further comprising adding water to the zilpaterol, propylene glycol mixture of step a).

9. The process of claim 7, wherein the zilpaterol solution of step b) is supersaturated with respect to zilpaterol.

10. The process of claim 7, wherein the mixture of step a) is heated to a temperature in the range of about 40° C. to about 100° C.

11. A method of preparing an animal feed comprising mixing the animal feed premix of claim 1 with grain.

12. The method of claim 11, wherein the relative standard deviation (RSD) value of the distribution of the zilpaterol in the feed prepared from the premix is less than 15%.

13. The method of claim 12, wherein the RSD of the distribution of the zilpaterol in the feed is less than 10%.

14. The method of claim 13, wherein the RSD of the distribution of the zilpaterol in the feed is less than 5%.

15. The method of claim 11, wherein the concentration of zilpaterol in the feed is 4 ppm or less.

16. A method of preparing an animal feed comprising mixing the animal feed premix of claim 6 with grain.

17. The method of claim 16, wherein the relative standard deviation (RSD) value of the distribution of the zilpaterol in the feed prepared from the premix is less than 15%.

18. The method of claim 16, wherein the RSD of the distribution of the zilpaterol in the feed is less than 10%.

19. The method of claim 16, wherein the RSD of the distribution of the zilpaterol in the feed is less than 5%.

20. The method of claim 16, wherein the concentration of zilpaterol in the feed is 4 ppm or less.

* * * * *